United States Patent
Li

(12) 
(10) Patent No.: US 6,743,930 B2
(45) Date of Patent: Jun. 1, 2004

(54) KERNEL OIL FROM PLANT KERNEL, PROCESS FOR EXTRACTING SAME, PHARMACEUTICAL COMPOSITION AND THEREOF

(76) Inventor: Dapeng Li, 11th Street (Xiasha) Economic & Technical Development Zone, Hangzhou, P. R. (CN)

( * ) Notice: Subject to any disclaimer, the term of this patent is extended or adjusted under 35 U.S.C. 154(b) by 72 days.

(21) Appl. No.: 10/123,964

(22) Filed: Apr. 16, 2002

(65) Prior Publication Data

US 2003/0195178 A1 Oct. 16, 2003

(51) Int. Cl.$^7$ .................................................. C07C 1/00
(52) U.S. Cl. ................. 554/12; 554/8; 554/9; 554/11; 554/16; 554/227; 514/547
(58) Field of Search ............................ 554/8, 9, 11, 12, 554/16, 227; 514/547

(56) References Cited

PUBLICATIONS

Senter et al., "GLC–MS Analysis of Fatty Acids from Five Black Walnut Cultivars", Journal of Food Science 47:1753–1755, 1982.

Senter et al., "Lipid Constituents of Black Walnut Kernels", Journal of Food Science 44:266–268, 1979.

Mehran, "Oil Characteriestics of Iranian Walnuts", Journal of the American Oil Chemists 51:477–478, 1974.

*Primary Examiner*—Deborah D. Carr
(74) *Attorney, Agent, or Firm*—Fish & Richardson, P.C.

(57) ABSTRACT

The invention provides a kernel oil extracted from plant kernels, comprising triglyceride 90–99.9%, diglyceride 0.01–5%, monoglycerides 0.01–3%, sitosterol 0.1–2.5% and cyclolanosterol 0.01–1%. The invention also provides two methods for the extraction of said kernel oil, the pharmaceutical compositions and the uses thereof.

29 Claims, No Drawings

KERNEL OIL FROM PLANT KERNEL, PROCESS FOR EXTRACTING SAME, PHARMACEUTICAL COMPOSITION AND THEREOF

FIELD OF THE INVENTION

The invention relates to natural pharmaceutical chemistry, especially relates to kernel oils extracted from plant kernels, more especially relates to kernel oils extracted from spine date (*Semen ziziphi spinosae*), flatspine pricklyash and walnut (*Semen persicae*), the process for preparing same, the pharmaceutical composition containing same and the medicinal use thereof.

BACKGROUND OF THE INVENTION

The spine date kernel and the flatspine pricklyash are Chinese traditional medicines for both medical- and food-purpose, which have functions such as nourishing liver, calming heart, constraining sweating, engendering liquid, warming the middle warmer to alleviate pain, killing parasites and relieving itch.

The walnut kernel is one of the Chinese traditional medicines for both medical- and food-purpose, and has functions of nourishing the kidney, warming the lung and moistening the bowel. However, walnut kernel oil has usually been used as an edible oil and has not been reported as a parenteral nutritional agent. The common walnut kernel oil preparation is not advantageous to human absorption, and its medical application is restricted since it is difficult for it to meet the clinic requirements as an intravenous emulsion. The backward technology of extraction and separation in the prior art induces in unqualified chemical and physical properties (such as acid value) and high impurity contents.

In the prior art, the fat emulsions prepared from the soya bean oil, the cotton seed oil and the red flower oil are commonly used to replenish nutrients and energy to human body. The fat emulsion made from soya bean oil is more widely used. However, no work on the improvement of immunological functions, the increase of serum proteins, the inhibition on transplanted tumor, experimental Lewis lung cancer and liver cancer HAC, and the functions of nourishing kidney, warming lung and loosening bowel has not been reported in the studies of the fat emulsion made from the soya bean oil.

Thus, the first aspect of the invention is to provide a kernel oil from kernels of plants which can be used for the preparation of a novel intravenous emulsion having functions of replenishing nutrients, improving immunologic function and increasing serum proteins.

The second aspect of the invention is to provide two special technological processes for the extraction of the kernel oil of the invention.

The third aspect of the invention is to provide a pharmaceutical composition containing the kernel oil of the invention, including intravenous emulsion and oral capsules. Said intravenous emulsion can replenish nutrients, improve immunologic function and increase serum proteins. Also, it has functions of nourishing kidney, warming lung and loosening bowel. In addition, it is not expensive.

The fourth aspect of the invention is to provide the use of the kernel oil of the invention in the preparation of remedies for the treatment of diseases such as tumors, AIDS and hypoimmunity, etc.

SUMMARY OF THE INVENTION

The kernel oil extracted from plant kernels according to the first aspect of the invention comprises triglycerides 90–99.9%, diglycerides 0.01–5%, monoglycerides 0.01–3%, sitosterol 0.1–2.5% and cyclolanosterol 0.01–1%.

One process for extracting the kernel oil of according to the invention comprises the steps of:

1) Crude extraction: the kernel/kernel powder being expressed or extracted with an organic solvent or via supercritical fluid extraction to obtain a crude oil;
2) Decoloring: decoloring the crude oil with an adsorbent decoloring agent to obtain a decolored oil;
3) Caustic refining: dissolving the decolored oil in petroleum ether, adding a stoichiometric amount of NaOH under agitation, standing still and demixing, then washing the organic phase, thus obtaining an emulsion;
4) Demulsifying: adding acetone into the emulsion with agitation, separating layers and achieving the upper layer of oil phase.
5) Adsorption and water-washing: Subjecting the oil phase to be adsorbed with neutral alumina and kaolin sequently, and filtered, then removing the organic solvent from the filtrate in nitrogen atmosphere, and washing the oil phase with worm water, drying, then adsorbing with neutral alumina, thus obtaining a refined oil.

Another process for extracting the kernel oil according to the invention comprises the steps of:

1) Crude extraction: the kernel/kernel powder being expressed or extracted with an organic solvent or via supercritical fluid extraction to obtain a crude oil;
2) Degumming: agitating and heating the crude oil, then adding phosphoric acid to render a complete reaction;
3) Caustic refining: adding NaOH or $Na_2CO_3$ solution at the same temperature into the degummed oil to render a complete reaction, then standing still and demixing, thus obtaining a refined oil;
4) Water-washing: washing the caustic-refined oil with pure water to obtain a water-washed oil.
5) Dewatering: adding an adsorbent into the water-washed oil or heating the water-washed oil under vacuum to remove the water, thus obtaining a clear dewatered oil;
6) Decoloring: decoloring the dewatered oil with an adsorbent decoloring agent to obtain a decolored oil;
7) Deodorizing: heating the decolored oil with agitation under vacuum in nitrogen atmosphere to raise the oil temperature to 120–160° C., feeding steam made from pure water into the oil and further heating the oil to 160–260° C. and keeping for 0.5–2 hours, then cutting short the pure water steam, thus removing the moisture from the oil and obtaining deodorized oil.

2. The pharmaceutical composition according to the invention comprises a therapeutically effective amount of the kernel oil extracted from kernels of plants and one or more pharmaceutically acceptable adjuvants.

The invention also provides the use of the kernel oil from kernels of plants in the preparation of remedies for treating tumors, AIDS, hypoimmunity, infantile malnutrition, post-operation and diseases in need of supplementing fat elements.

DETAILED DESCRIPTION OF THE INVENTION

The kernel oil extracted from plant kernels according to the invention is a clear light yellow oily liquid which comprises triglycerides 90–99.9%, diglycerides 0.01–5%, monoglycerides 0.01–3%, sitosterol 0.1–2.5% and cyclolanosterol 0.01–1%.

The lipolysis of said kernel oil gives the following fatty acids: hexadecanoic acid 5–8%, octadecanoic acid 1–3%, octadecenic acid 18–30%, octadecadienoic acid 50–65% and calendic acid 6–14%.

The kernel oil of the invention possesses the following physical properties examined on the basis of fatty oil: relative density 0.920–0.930, refractive index 1.470–1.480, acid value<0.80, iodine value 120.0–155.0, saponification value 180.0–200.0, peroxide value<30.0 meq.kg$^{-1}$, ignited residue 0.01–0.04%, arsenic salts<2 ppm, heavy metals<10 ppm, and mean molecular weight 873.96.

The preferred embodiments of the kernel oils of the invention are those extracted from kernels of spine date, flatspine pricklyash and walnut.

With the walnut kernel as an example, the first process for extracting kernel oils includes the following steps:

Primary extraction—The kernel/kernel powder being expressed or extracted with an organic solvent or via supercritical fluid extraction to obtain a crude walnut kernel oil;

Decoloring—Adding proper amount of petroleum ether into the crude oil and thoroughly mixing it, adding proper amount of activated carbon for injection-purpose, keeping the temperature constant, filtering the mixture, and recovering the petroleum ether, thus obtaining a decolored oil;

Caustic refining—Putting the decolored oil and a proper amount of petroleum ether into a reaction kettle, adding 2% NaOH in an amount calculated on basis of the acid value and the amount of the decolored oil with agitation, standing still, and removing the lower layer of liquid waste, then adding two fold of warm distilled water with agitation, standing still, and removing the lower layer of liquid waste, then washing once more in the same method, duration and water temperature as above, sufficiently standing still, removing the lower layer of liquid waste, and obtaining the upper layer of emulsion;

Demulsifying—Metering and transferring the emulsion layer into a separator, and filling acetone in a given ratio to the amount of emulsion layer with constant agitation, after standing still and separating layers, removing the lower layer of liquid waste, thus obtaining the upper layer of oil phase.

Water-washing—Adding the neutral heat-activated alumina in an amount based on the oil amount to conduct the adsorption, mixing thoroughly, standing still and filtering to obtain a clear oil, then preheating the metered clear oil in a reaction kettle, adding necessary amount of the heat-activated white bole (kaolin) with agitation and heat preservation, filtering under vacuum, heating the filtrate in a washing vessel, removing the organic solvent in nitrogen atmosphere, filling warm distilled water in an amount base on the oil amount, mixing thoroughly, standing still, and removing the lower layer of liquid waste, then heating the oil layer in nitrogen atmosphere to dewater and dry it until the oil layer becomes clear, then adding neutral activated alumina in an adequate amount, mixing thoroughly, standing still, and making sterile filtration, thus obtaining a refined oil.

The purpose of protection with nitrogen in the above process is mainly for improving oil quality through preventing the fat from oxidation and controlling fat's peroxide value.

If desired, the kernel oil from walnut obtained above can further be packed and sterilized. Then it can be filled into specified containers and sterilized, thus a kernel oil for injection is obtained.

The second process for extracting the kernel oil of the invention includes the following steps:

1) Crude extraction: the kernel/kernel powder being expressed, or extracted via supercritical fluid extraction to obtain a clear crude oil;

2) Degumming: Putting the crude oil into a reaction kettle, filling nitrogen, agitating, heating, adding a proper amount of phosphoric acid, and agitating fast to render a complete reaction;

3) Caustic refining: Directly adding NaOH or $Na_2CO_3$ solution with the same temperature into the degummed oil mixture in nitrogen atmosphere, agitating fast to enable free fatty acids to react completely, then standing still to separate layers in the condition of heating and filling nitrogen, and removing the soapstock to obtain a refined oil.

4) Water-washing: Adding proper amount of sodium chloride solution into the caustic-refined oil under agitating, standing still to separate layers with the keeping of temperature, and removing the lower layer of liquid waste, then washing twice with pure water in the same method, duration and water temperature as above, standing still to separate layers and removing the lower layer of liquid waste to obtain a water-washed oil;

5) Dewatering: Adding proper amount of activated alumina into the water-washed oil, mixing thoroughly, standing still and filtering the mixture to obtain a clear dewatered oil;

6) Decoloring: Adding the dewatered oil into a stainless steel reaction kettle, mixing and heating the oil up to 140° C. with agitation under vacuum in nitrogen atmosphere, adding proper amount of a mixture of activated carbon and activated kaolin, agitating thoroughly under vacuum at 80–90° C., cooling, and filtering the mixture thus obtaining a decolored oil.

7) Deodorizing: Adding the decolored oil into a stainless steel reaction kettle, heating the decolored oil up to 140° C. with agitation under vacuum in nitrogen atmosphere, then feeding steam made from pure water in stead of nitrogen, and further heating the oil up to 190° C. and keeping the same temperature for 1.5 hours, then cutting short the pure water steam, and agitating in nitrogen atmosphere again, then cooling the oil to obtain a deodorized oil.

If desired, the obtained deodorized oil can further be sterilized, i.e., the deodorized oil is introduced into a stainless steel sterilizing vessel and heated up to 160° C. with agitation under vacuum. After keeping at this temperature for 2 hours, the oil is cooled down and aseptically filtrated, then filled into containers in nitrogen atmosphere and sealed, thus obtaining a kernel oil for injection.

The pharmaceutical composition according to the invention comprises a therapeutically effective amount of the kernel oil of the invention extracted as above and one or more pharmaceutically acceptable adjuvants.

The pharmaceutically acceptable adjuvants in the composition of the invention include one or more substances selected from a group consists of an emulsifier, a solubiliser, a latent solvent, an isotonic regulator, an antioxidant and an stabilizer.

The pharmaceutical composition of the invention can further comprise other active drugs selected from anti-tumor agents, anti-AIDS agents, immunomodulators and nutrients.

The pharmaceutical composition of the invention can further comprise one or more vegetable oils, e.g., copra oil, peanut oil, etc.

The pharmaceutical composition of the invention can be a fatty emulsion, such as an intravenous fat emulsion or an oral fat emulsion. It can also be a soft capsule or an iodine oil, etc.

One of the preferred embodiments of the pharmaceutical composition of the invention is a fatty emulsion, wherein said pharmaceutically acceptable adjuvants are an emulsifier and an isotonic regulator. More preferred embodiment is an intravenous fatty emulsion of walnut kernel oil.

Preferably, the intravenous fatty emulsion of walnut kernel oil contains, based on the total volume of the emulsion of 100 ml, from 5 g to 30 g, more preferably from 10 g to 30 g, most preferably 20 g of parenteral walnut kernel oil (walnut kernel oil for injection).

The emulsifier used in this invention can be phosphatide (including soya lecithin, yolk lecithin and soya phosphatide), Pluronic, polyglyceryl dipalmitate, etc. It is preferable to use natural emulsifiers, e.g., soya lecithin or yolk lecithin, in the intravenous fatty emulsion in an amount, based on the total volume of the emulsion of 100 ml, of bout 1.0–3.0 g, more preferable, 1.0–2.0 g, and most preferably, 1.2 g.

The isotonic agent used in the invention can be glycerin, sorbitol, xylitol and glucose, etc., preferably, glycerin in an amount, based on the total volume of the emulsion of 100 ml, from 1.5 g to 3.0 g, more preferably, 2.5 g.

The invention is further described with examples, which are presented for purpose of illustration and by no way of limitation to the invention.

EXAMPLES

Example 1

1000 g of walnut kernels were expressed and 450 g of cruel walnut kernel oil were obtained.

Petroleum ether in an amount of ca. 40% crude oil amount was added into the crude oil and mixed thoroughly, then activated carbon in an amount of ca. 1% crude oil was added. After keeping at 45° C. for 30 minutes, the mixture was filtered, and the petroleum ether was recovered from the filtrate, thereby 428 g of decolored oil was obtained.

The decolored oil and petroleum ether in ca. 50% of the decolored oil were fed into a reaction kettle, and 307 ml 2% NaOH, based on the acid value and the amount of the decolored oil, was filled in a fine stream into the emulsion layer with agitation. The mixture was agitated for another 10 minutes and remained still for 24 hours, then the lower layer of liquid waste was removed. Two fold of distilled water in a temperature of 45° C. was added with agitation, then the mixture remained still for 24 hours, and the lower layer of liquid waste was removed. The second washing was carried on in the same method, duration and water temperature as above, except the amount of water was about 1.5 times of the amount of emulsion layer, then remained still for 48 hours.

The lower layer of liquid waste was removed and 342 g of upper layer of emulsion were obtained. The emulsion layer was transferred into a separator, and 342 ml of acetone were added rapidly with agitation. After remaining still for 3 hours, the lower layer of liquid waste was removed, and the upper layer of oil phase was obtained.

Alumina activated by heating at the temperature of 160° C. for 2 hours was added at a rate of ca. 5% of the amount of oil into the oil phase, and the contents were mixed thoroughly. After standing still for 30 minutes, the mixture was filtered to obtain a clear oil. The clear oil was metered and taken into a reaction kettle therein the oil was preheated to 40° C. White bole (kaolin) activated by heating at the temperature of 160° C. for 2 hours was added at a rate of ca. 3% of the amount of oil with agitation, and the mixture was kept at 50° C. with agitation for 30 minutes, then filtered under vacuum, and the filtrate was fed into a washing vessel and heated to 60° C. The organic solvent was removed in nitrogen atmosphere, and distilled water of 45° C. was filled fast at an amount equal to that of the oil. After being agitated for additional 15 minutes and standing still for 30 minutes, the lower layer of liquid waste was removed. The oil layer was heated to 80° C. in nitrogen atmosphere to remove water and dried until the oil layer became clear. Activated neutral alumina was added, and the mixture was agitated thoroughly, followed by standing still. A refined oil was obtained via aseptic filtration.

The refined oil obtained as above was filled into specified containers and the sterilization was conducted, thus 328 g of parenteral walnut kernel oil were obtained.

Example 2

1. Crude extraction: 30 kg of walnut kernel were expressed to obtain a crude oil, then the crude oil was filtered to obtained 13.1 kg of clear crude oil.

2. Degumming: The crude oil was put into a reaction kettle, and heated to a temperature from 30 to 35 with agitation in nitrogen atmosphere. 13.1 g of 85% Phosphoric acid were added into the oil, and the mixture was agitated fast for 0.5 hour.

3. Caustic refining: 717 g of 5% NaOH solution in the same temperature as above was added directly into the degummed oil in nitrogen atmosphere, the mixture was agitated fast for 30 minutes, then heated rapidly to a temperature from 60 to 65 with slow agitation. The slow agitation continued for 15 minutes, then stopped. After standing still at the same temperature in nitrogen atmosphere, layers separated. The soapstock was removed and 12.8 kg of refined oil was obtained.

4. Water-washing: 1.9 kg of 0.2% Sodium chloride solution in the same temperature was added into the above caustic-refined oil with agitation. The mixture was remained still and layers were separated under heat preservation. The lower layer of liquid waste was discarded. Wash was conducted twice in the same method, duration and water temperature, except in replace of sodium chloride solution with purified water. After standing still, layers were separated. The lower layer of liquid waste was discarded, and 12.6 kg of water-washed oil was obtained.

5. Dewatering: 1.3 kg of Alumina activated at 160° C. for 2 hours was added into the above water-washed oil. The mixture was agitated thoroughly, remained still for at least 0.5 hour, then filtered, thus 12.0 kg of clear dewatered oil was obtain.

6. Decoloring: The above decolored oil was added into a reaction kettle and heated to 80 to 90° C. with agitation under vacuum of 0.082 Mpa. A mixture of 22.5 g of activated carbon and 337.5 g of kaolin activated at 160° C. for 2 hours was added in normal pressure. The mixture was agitated thoroughly for 20 minutes at 80–90° C. under vacuum of 0.082 MPa, then cooled down to 40° C. and filtered. Thus, 11.0 kg of decolored oil was obtained.

7. Deodorizing: The above decolored oil was put into a stainless steel reaction kettle, and heated to 140° C. with agitation under vacuum of 0.082 Mpa. Then pure water steam was fed instead of nitrogen, and the oil was further heated to 190° C. The temperature was preserved for 1.5 hours for heat preservation. Then the steam was cut off and nitrogen was fed again with agitation. After cooling down, 10.6 kg of deodorized oil was obtained.

8. Sterilizing: The deodorized oil was put into a sterilizing vessel, and heated to 160° C. with agitation under vacuum of 0.082 MPa. This temperature was kept for 2 hours, then the oil was cooled down, sterile filtrated, packed and filled with nitrogen, and the containers were sealed. Thus, 9.6 kg of parenteral walnut kernel oil was obtained.

| Formula example 1 | |
|---|---|
| Walnut kernel oil for injection | 5–30 g |
| Lecithin for injection | 1.0–3.0 g |
| Glycerin for injection | 1.5–3.0 g |
| Vitamin E | 0–0.15 g |
| Water for injection | to 100 ml |
| Formula example 2 | |
| Walnut kernel oil for injection | 20 g |
| Soya lecithin for injection | 1.2 g |
| Glycerin for injection | 2.5 g |
| Water for injection | to 100 ml |
| Formula example 3 | |
| Fluorouracil | 1.0–5.0 g |
| Walnut kernel oil for injection | 5.0–30 g |
| Soya lecithin for injection | 1.0–3.0 g |
| Glycerin for injection | 1.5–3.0 g |
| Vitamin E | 0–0.15 g |
| Water for injection | to 100 ml |
| Formula example 4 | |
| Paclitaxel (Taxol) | 10–60 mg |
| Copra oil | 5–15 g |
| Walnut kernel oil for injection | 5–15 g |
| Lecithin for injection | 1.0–3.0 g |
| Glycerin for injection | 1.5–3.0 g |
| Vitamin B | 0–0.15 g |
| Water for injection | to 100 ml |
| Formula example 5 | |
| Paclitaxel (Taxol) | 10–60 mg |
| Polyoxyethylenated castor oil | 1–5 g |
| Walnut kernel oil for injection | 5–30 g |
| Lecithin for injection | 1.0–3.0 g |
| Glycerin for injection | 1.5–3.0 g |
| Vitamin E | 0–0.15 g |
| Water for injection | to 100 ml |
| Formula example 6 | |
| Homoharringtonine | 0.05–0.2 g |
| Walnut kernel oil for injection | 5.0–30 g |
| Soya lecithin for injection | 1.0–3.0 g |
| Glycerin for injection | 1.5–3.0 g |
| Vitamin E | 0–0.15 g |
| Water for injection | to 100 ml |
| Formula example 7 | |
| Cyclophosphamide | 0.2–1.2 g |
| Walnut kernel oil for injection | 5.0–30 g |
| Lecithin for injection | 1.0–3.0 g |
| Glycerin for injection | 1.5–3.0 g |
| Vitamin E | 0–0.15 g |
| Water for injection | to 100 ml |

Example 3

1.2 g of soya lecithin and 2.5 g of glycerin were added into 25 ml of water. The mixture was agitated at 5,000 rpm to form a homogenous translucent colloidal dispersion, then 20 g of walnut kernel oil for injection was added, and water was added to a total volume of 100 ml, thus a primary emulsion was formed. The pH value of the primary emulsion was regulated into 6–9 with NaOH solution, then transferred into a homogenizing vessel. The emulsion was homogenized at a low pressure—10~20 Mpa and a high pressure—40~60 MPa, respectively, at a temperature from 60 to 80° C. The homogenization was repeated 6 times in the same conditions as above. The emulsion obtained was filtered, filled and sterilized to give a 20% intravenous walnut kernel fatty emulsion.

Example 4

1.0 g of yolk lecithin and 1.5 g of glycerin were added into 20 ml of water. The mixture was agitated at the speed as above to form a homogenous translucent colloidal dispersion, then 10 g of walnut kernel oil for injection was added, and water was added to a total volume of 100 ml, thus a primary emulsion was formed. The primary emulsion was regulated into pH 6–9, homogenized, filtered, filled and sterilized to give a 10% intravenous walnut kernel fatty emulsion.

Example 5

2.0 g of soya lecithin and 3.0 g of glycerin were added into 30 ml of water. The mixture was agitated at the above speed to form a homogenous translucent colloidal dispersion, then 30 g of walnut kernel oil for injection was added and water was added to a total volume of 100 ml, thus a primary emulsion was formed. The primary emulsion was regulated into pH 6–9, homogenized, filtered, filled and sterilized to give a 30% intravenous walnut kernel fatty emulsion.

Example 6

A fatty emulsion in formula 3 was obtained in the same manner as Example 3 except that fluorouracil was dissolved first in an adequate amount of water.

Example 7

A fatty emulsion in formula 4 was obtained in the same manner as Example 3 except that paclitaxel was dissolved first in copra oil and then mixed with walnut kernel oil for injection.

Example 8

A fatty emulsion in formula 5 was obtained in the same manner as Example 3 except that paclitaxel was dissolved first in polyoxyethylenated castor oil and then mixed with walnut kernel oil for injection.

Example 9

A fatty emulsion in formula 6 was obtained in the same manner as Example 3 except that homoharringtonine was dissolved first in an adequate amount of water.

Example 10

A fatty emulsion in formula 7 was obtained in the same manner as Example 3 except that cyclophosphamide was added together with soya lecithin and glycerin into wter and homogenized..

Example 11

Oral capsules of the invention were prepared as follows:
0.675 g of Vitamin E, as an antioxidant, was dissolved in 900 g of kernel oil of spine date, flatspine pricklyash or walnut with agitation at room temperature to give a clear and transparent solution.

Gelatin, water, glycerin, and conserving agent were weighed at a rate of 1:1:0.4:0.001. The better of distilled water was added into a reaction kettle and heated to a temperature from 50 to 60° C., then gelatin, glycerin and conserving agent were added with agitation. The containers were washed with the remaining distilled water, and the washings were poured into the kettle. The mixture in the kettle was gradually heated until being completely dissolved and homogenized, then the reaction kettle was closed and a vacuum pump was operated to keep a gauge pressure of 0.065–0.080 Mpa for 30–60 minutes. The slurry was filtered through a 120 mesh screen into to storage vessel and kept at a temperature from 50 to 60° C.

1000 Capsules were prepared by pressing with 8# molds in the following conditions: room temperature 21–24° C., relative humity<40%, glue chamber temperature 50–60° C., divider voltage 110–150 V, glue band temperature 10–15° C., glue line thickness 0.8–1.0 mm. The load amount of the contents was regularly inspected. 4 Hours after pressing, the capsules were wiped to remove oil, and baked for 8 hours, then washed with petroleum ether (30–50° C.) and baked again. After picking out unqualified ones, the capsules were packed.

Test Example 1

40 mice of Kunming species, body weight 19–21 g, half male and half female, were injected via tail vein the emulsion of the invention, 0.5 ml/20 g body weight. The injection was repeated three times a day at intervals of 4 hours. The maximum tolerance dose is 75 ml/kg body weight. The animals were observed for 7 days. No inverse effect or death was observed during the period of test, and no abnormality was found in organs in anatomy.

Hemolytic tests were conducted in conventional methods for examining hemolytic action. No hemolysis was observed. The allergometry on guinea pigs did not show obvious anaphylaxis caused by the emulsion of the invention.

Rabbits were injected slowly, via ear edge vein, the emulsion of the invention at a dose of 15 ml/kg and 5 ml/kg, respectively, once a day for 7 days. No obvious irritation on rabbits' ear edge vein was shown.

Test Example 2

The heat value of the walnut kernel oil of the invention, measured according to GB384-81, is 37599 KJ/kg, equivalent to that of Soya bean (37243 KJ/kg), and the heat value of the walnut kernel oil emulsion is 6303 KJ/kg.

Test Example 3

Tests of Anoxia Tolerance and Fatigue Endurance in Mice 40 male healthy mice were divided randomly into 4 groups on basis of body weights, 10 for each. Three groups accepted walnut kernel oil emulsion in doses of 25 ml/kg, 12.5 ml/kg and 6.25 ml/kg, respectively. A normal saline (NS) group accepted same volume of normal saline. All the test materials were injected via tail vein, once a day for 7 days, and tests were conducted 2 hours after the last injection.

Test of Anoxia Tolerance

Each tested mouse was put in a 250 ml colorless wide mouth bottle containing 10 g of sodium lime. The duration was metered from the time the mouse was put into the bottle till its aspiration stopped. The mean survival times (min) were calculated and the differences between the emulsion groups and the normal saline group were compared.

Test of Fatigue Endurance

The mice were weighed respectively. Each mouse was loaded a weight of 5% of the body weight at its tail and immersed into a big vat in which the water temperature is 25° C. and the water depth is 40 cm. The mice were forced to swim till they sank to the bottom and died. The swimming duration for each mouse was recorded (min). Data were analysed statistically using t-test. The differences between each emulsion groups and normal saline were compared.

TABLE 1

Effects of walnut kernel oil emulsion, iv., in different doses on anoxia tolerance and fatigue endurance in mice

| Group | Dose (ml/kg) | Load-swimming test | | Tests of anoxia tolerance in atmospheric pressure | |
|---|---|---|---|---|---|
| | | Lasting duration (min) (x ± SD) | Prolongation ratio (%) | Survival time (min) (x ± SD) | Prolongation ratio (%) |
| NS | | 9.18 ± 5.0 | | 30.46 ± 5.33 | |
| Walnut kernel oil emulsion | 6.25 | 18.13 ± 16.64 | 97.58 | 34.91 ± 7.59 | 14.61 |
| | 12.5 | 19.96 ± 9.65** | 17.56 | 41.77 ± 9.38** | 37.13 |
| | 25 | 22.88 ± 7.89** | 149.31 | 43.73 ± 5.37** | 43.56 |

Compared with normal saline, *p < 0.05, **p < 0.01

The test results are shown in table 1. The statistic analysis of anoxia tolerance test shows an extremely significant difference between the mean survival times of the mice injected with walnut oil emulsion at both high and middle doses and those of the mice injected with normal saline ($p<0.01$). The above results also show that the effects of anoxia tolerance and nonspecific ergotropy of the walnut oil emulsion are dose-dependent in mice.

The statistic analysis of load-swimming test shows an extremely significant difference between the lasting durations of the mice injected with walnut oil emulsion at both high and middle doses and those of the mice injected with normal saline ($p<0.01$). The above test shows that the walnut oil emulsion at a dose of 25 ml/kg has a remarkable dose-dependent prolongation on the swimming duration and a remarkable dose-dependent enhancement of fatigue durance.

Test Example 4

Effects on Immune Functions in Mice

Effects on Proliferation of Lymphocyte

30 C57BL/6 mice were randomly divided into 5 groups (6 for each): walnut kernel oil emulsion 25 ml/kg, 12.5 ml/kg and 6.25 ml/kg; Intralipid 12.5 ml/kg; and normal saline (0.5 ml/mouse). All were administrated intravenously, once a day for 7 days. The animals were sacrificed after the last administration, the spleens were picked out in aseptic condition and the splenocyte suspensions were prepared.

The splenocytes were counted, and regulated into a concentration of $1\times10^7$ cells/ml. Into each hole of the 96-hole microtiter plate, 100 µl of cell suspension, 50 µl ConA and 50 µl of RPMI-1640 medium were added in triplicate. The plate was incubated for 48 hours at 37° C., with 5% $CO_2$. Then, $^3$H-TdR was added in 0.5 µci/hole, and the plate was incubated for additional 18 hours. Cells were collected with a multi-head cell collector and CPM values were counted with a liquid scintillation counter. Data were compared between the Intralipid group and the normal saline group, and between treatment groups and the control groups.

Effects on the Activity of NK Cells in Mice

30 C57BL/6 mice were randomly divided into 5 groups (6 for each): walnut kernel oil emulsion 25 ml/kg, 12.5 ml/kg and 6.25 ml/kg; Intralipid 12.5 ml/kg; and normal saline (0.5 ml/mouse). All were administrated intravenously, once a day for 7 days. The animals were sacrificed after the last administration, the spleens were picked out in aseptic condition and the splenocyte suspensions were prepared.

The splenocyte suspensions were regulated, with RPMI-1640 medium (produced by Difco, containing 15% of bovine serum, mercaptoethanol, Hepes, etc.), into a concentration of $1 \times 10^6$ cells/ml, as effector cells.

YAC-1 cells which had been incubated for 24 hours were regulated, with RPMI-1640 medium, into a concentration of $1 \times 10^4$ cells/ml, as target cells.

100 µl of the effector cells and 100 µl of the target cells were added into the holes of a 96-hole microtiter plate, and 0.5 µci of $^3$H-TdR was added in each hole. The tests were triplicated. The plate was incubated in the condition of 37° C. and 5% $CO_2$ and the cells were achieved. CPM values were determined and specific inhibition percentages (Pi), which represent the activity of NK cells, were calculated.

$$Pi = 1 - \frac{\text{CPM value of treatment group}}{\text{CPM value of control group}} \times 100\%$$

Effects on IL-2 in Mice

30 C57BL/6 mice were divided randomly into 5 groups (6 for each): walnut kernel oil emulsion 25 ml/kg, 12.5 ml/kg and 6.25 ml/kg; Intralipid 12.5 ml/kg; normal saline (0.5 ml/mouse). All were administrated intravenously, once a day for 7 days. The animals were sacrificed after the last administration, the spleens were picked out in aseptic condition and the splenocyte suspensions were prepared.

The splenocyte suspensions were regulated, with RPMI-1640 medium (produced by Difco, containing 15% of bovine serum, mercaptoethanol, Hepes, etc.), into a concentration of $1 \times 10^7$ cells/ml.

2 ml of cells and 5 µg/ml of ConA were added into each hole of a 24-hole plate. The plate was incubated in the condition of 37° C. and 5% $CO_2$ for 24 hours, then the supernatant was collected. The activity of IL-2 was determined by $^3$H-TdR incorporating method using IL-2 dependent clone CTLL. 100 µl of CTLL cell suspension in $1 \times 10^5$ cells/ml, 20 µl of $^3$H-TdR and 100µ of supernatant were added into each hole of a 96-hole microtiter plate. CPM values were determined and the differences were compared between treatment groups and the control.

TABLE 2

Effect of walnut kernel oil emulsion, iv., in different doses on immune functions in mice

| Group | Dose (ml/kg) | Lymphocyte proliferation (CPM)(x ± SD) | IL-2 (CPM) (x ± SD) | NK activity Pi(%) |
|---|---|---|---|---|
| Normal saline | 25 | 6049 ± 459 | 750 ± 112 | |
| Intralipid | 12.5 | 6248 ± 209 | 751 ± 96* | 1.2 |
| Walnut kernel oil emulsion | 6.25 | 8913 ± 911** | 941 ± 103** | 27.9 |
| | 12.5 | 8988 ± 1374** | 875 ± 160** | 43.8 |
| | 25.0 | 8480 ± 1283** | 917 ± 30** | 31.9 |

*p > 0.5, Compared between Intralipid (soya oil emulsion) and normal saline.
**p < 0.01, Compared between walnut kernel oil emulsion and normal saline, Compared between walnut kernel oil emulsion and Intralipid.

The above results shows that the walnut kernel oil emulsion, iv., at a dose of 25, 12.5 or 6.25 ml/kg 7 day can obviously promote lymphocyte prolifiration, activate the activity of natural killing cells (NK cells) and promote the formation of IL-2 in mice, i.e., the effects of the emulsion of the invention on immune functions are significantly superior to those of the soya oil emulsion.

Test Example 5

40 mice were divided randomly into 4 groups. The animals were injected normal saline 10 ml/kg, walnut kernel oil emulsion 6.25 ml/kg, 12.5 ml/kg and 25 ml/kg, respectively, i.v., 7 day. The animals were sacrificed after the last administration, and the blood samples were collected for the examination of total serum proteins. The results are shown in Table 3.

TABLE 3

Effect of walnut kernel oil emulsion on total serum proteins in mice

| Group | Dose (ml/kg) | Total serum proteins (g/L) (x ± SD) |
|---|---|---|
| Normal saline | 10 | 69.8 ± 8.7 |
| Walnut kernel oil emulsion | 6.25 | 85.4 ± 14.0** |
| | 12.5 | 86.1 ± 10.4** |
| | 25 | 79.8 ± 7.4** |

*p < 0.05, **p < 0.01, Compared with normal saline.

Test Example 6

Inhibitions on HAC Hepatic Cancer and Lewis Lung Cancer in Mice

Well-grown HAC peritoneal fluids were collected, and diluted with normal saline in a ratio of 1:4 to prepare cell suspensions. Every mouse was inoculated subcutaneously 0.2 ml of the cell suspension at the oxter. The animals were divided randomly into 4 groups: normal saline group and groups of walnut kernel oil emulsion, 25 ml/kg, 12.5 ml/kg and 6.25 ml/kg. The administration began next day, i.v.,×7 days. Ten days after the inoculation, animals were sacrificed by dislocation of cervical spine. Tumors were picked up and the weights of tumor were compared. Tumor inhibition ratios were calculated by using the following formula and the results are shown in Table 4.

$$\text{Inhibition ratio \%} = \frac{\text{Weight of tumor}_{cont.} - \text{Weight of tumor}_{treat.}}{\text{Weight of tumor}_{cont.}} \times 100\%$$

TABLE 4

Inhibition of walnut kernel oil emulsion on HAC hepatic cancer in mice

| Group | Dose (ml/kg) | Number of animal | | Body weight of animal (g) | | Tumor weight (g) (x ± SD) | Tumor inhibition ratio (%) |
|---|---|---|---|---|---|---|---|
| | | Initial | Final | Initial | Final | | |
| Normal saline | 10 | 10 | 10 | 19.2 | 26.5 | 2.48 ± 0.31 | |
| Walnut kernel oil emulsion | 6.25 | 10 | 10 | 19.1 | 25.5 | 1.92 ± 0.35** | 22.58 |
| | 12.5 | 10 | 10 | 19.4 | 24.9 | 1.83 ± 0.39** | 26.21 |
| | 25 | 10 | 10 | 19.4 | 24.5 | 1.45 ± 0.22** | 41.53 |

**p < 0.01, compared with normal saline.

Well-grown tumor massae of Lewis lung cancer were collected, and homogenized with normal saline in a ratio of 1:4 to prepare cell suspensions. Every mouse was inoculated subcutaneously with 0.2 ml of the cell suspension at the oxter. The animals were divided randomly into 4 groups:

normal saline group and groups of walnut kernel oil emulsion, 25 ml/kg, 12.5 ml/kg and 6.25 ml/kg. The administration began next day, i.v., ×7 days. Ten days after the inoculation, animals were sacrificed by dislocation of cervical spine. Tumors were picked up and the weights of tumor were compared. The tumor inhibition ratios were calculated by using the following formula and the results are shown in Table 5.

$$\text{Inhibition ratio \%} = \frac{\text{Weight of tumor}_{cont.} - \text{Weight of tumor}_{treat.}}{\text{Weight of tumor}_{cont.}} \times 100\%$$

TABLE 5

Inhibition of walnut kernel oil emulsion on Lewis lung cancer in mice

| Group | Dose (ml/kg) | Number of animal Initial | Number of animal Final | Body weight of animal (g) Initial | Body weight of animal (g) Final | Tumor weight (g) (x ± SD) | Tumor inhibition ratio (%) |
|---|---|---|---|---|---|---|---|
| Normal saline | 25 | 6 | 6 | 18.5 | 24.4 | 2.25 ± 0.30 | |
| Walnut kernel oil emulsion | 6.25 | 6 | 6 | 18.1 | 23.5 | 1.87 ± 0.39 | 17.04 |
| | 12.5 | 6 | 6 | 18.6 | 22.9 | 1.63 ± 0.40* | 27.41 |
| | 25 | 6 | 6 | 18.4 | 22.5 | 1.27 ± 0.18** | 43.70 |

**p < 0.01, compared with normal saline.

It was shown from Table 4 and table 5 that the walnut kernel oil emulsion in the above doses inhibited HAC hepatic cancer and Lewis lung cancer in mice to some extent.

It was found in further investigations that the emulsion made from the walnut kernel oil also had the above functions when it was used as an energy agent. It may be attributed to its functions of nourishing kidney, warming lung and loosening bowel.

Utilities

The parental emulsion of the walnut kernel oil of the invention is formulated reasonable and the emulsifier used is safe and reliable. In addition to the functions of the supplement of nutrients and energy, the anoxia tolerance and the fatigue endurance, the increase of immune functions and increase of total serum proteins, it also inhibits HAC hepatic cancer and Lewis lung cancer in mice to some extent. Moreover, it possesses the functions of nourishing kidney, warming lung and loosening bowel, which are possessed by the raw material thereof. It is an energetic emulsion with various efficiencies, and can be used to treat tumors, venerisms, AIDS, hypoimmunity, infantile malnutrition, post-operation and diseases in need of supplementing fat elements.

The kernel oils extracted by the method of the invention have good quality with a high yield and possess desired medical effects. Especially, by introducing nitrogen in the extraction process to protect the oil from oxidation, the quality of the kernel oils has been raised effectively.

The biggest merit of the second method of the invention is that no organic solvent is used, so as to avoid pollution. The peroxide value of the kernel oil extracted can reach to less than 6.0 meq.kg$^{-1}$ by using said method.

What is claimed is:

1. A kernel oil extracted from plant kernels, comprising triglycerides 90–99.9%, diglycerides 0.01–5%, monoglycerides 0.01–3%, sitosterol 0.1–2.5% and cyclolanosterol 0.01–1%.

2. A kernel oil of claim 1, characterized in that the lipolysis of said kernel oil gives the following fatty acids: hexadecanoic acid 5–8%, octadecanoic acid 1–3%, octadecenic acid 18–30%, octadecadienoic acid 50–65% and calendic acid 6–14%.

3. A kernel oil of claim 1, characterized in having the following physical properties tested on the basis of fatty oil: relative density 0.920–0.930, refractive index 1.470–1.480, acid value<0.80, iodine value 120.0–155.0, saponification value 180.0–200.0, peroxide value<30.0 meq.kg–1, ignited residue 0.0 1–0.04%, arsenic salts<2 ppm, heavy metals<10 ppm, and mean molecular weight 873.96.

4. A kernel oil of claim 1, characterized in that the oil is extracted from kernels of spine date, flatspine pricklyash, or walnut.

5. A kernel oil of claim 1, isolated by a process comprising the steps of:
   1) Crude extraction: the kernel/kernel powder being expressed or extracted with an organic solvent or via supercritical fluid extraction to obtain a crude oil;
   2) Decoloring: decoloring the crude oil with an adsorbent decoloring agent to obtain a decolored oil;
   3) Caustic refining: dissolving the decolored oil in petroleum ether, adding a stoichiometric amount of NaOH under agitation, standing still and demixing, then washing the organic phase, and obtaining an emulsion; p1 4) Demulsifying: adding acetone into the emulsion under agitation, separating layers and achieving the upper layer of oil phase,
   5) Adsorption and water-washing: Subjecting the oil phase to be adsorbed with neutral alumina and kaolin sequently, and filtered, then removing the organic solvent from the filtrate under nitrogen atmosphere, and washing the oil phase with worm water, drying, then adsorbing with neutral alumina, thus obtaining a refined oil.

6. A kernel oil of claim 1, isolated by a process comprising the steps of:
   1) Crude extraction: the kernel/kernel powder being expressed or extracted with an organic solvent or via supercritical fluid extraction to obtain a crude oil;
   2) Degumming: agitating and heating the crude oil, adding phosphoric acid to render a complete reaction;
   3) Caustic refining: adding NaOH or Na2CO3 solution with the same temperature into the degummed oil to render a complete reaction, then standing still and demixing, thus obtaining a refined oil;
   4) Water-washing: washing the caustic-refined oil with pure water to obtain a water-washed oil,
   5) Dewatering: adding an adsorbent into the water-washed oil or heating the water-washed oil under vacuum to remove the water, thus obtaining a clear dewatered oil;
   6) Decoloring: decoloring the dewatered oil with an adsorbent decoloring agent to obtain a decolored oil;
   7) Deodorizing: heating the decolored oil under vacuum and agitation in nitrogen atmosphere to raise the oil temperature up to 120–160° C., feeding steam made from pure water into the oil and further heating the oil to 160–260° C. and keeping for 0.5–2 hours, then cutting short the pure water steam, thus removing the moisture from the oil and obtaining deodorized oil.

7. A pharmaceutical composition, comprising a therapeutically effective amount of the kernel oil of claim 1 and one or more pharmaceutically acceptable adjuvants.

8. A pharmaceutical composition of claim 7, further comprising one or more active drugs selected from antitumor agents, anti-AIDS agents, immunomodulators and nutrients.

9. A pharmaceutical composition of claim 7, further comprising one or more vegetable oils.

10. A pharmaceutical composition of claim 7, characterized in that said pharmaceutical composition is a fatty emulsion of a kernel oil extracted from plant kernels, comprising triglycerides 90–99.9%, diglycerides 0.01–5%, monoglycerides 0.01–3%, sitosterol 0.1–2.5% and cyclolanosterol 0.01–1%, and said phannaceutically acceptable adjuvants include one or more substances selected from a group consists of an emulsifier, a solubiliser, a latent solvent, an isotonic regulator, an antioxidant and an stabilizer.

11. A pharmaceutical composition of claim 10, comprising:

| | |
|---|---|
| Walnut kernel oil for injection | 5–30 g |
| Lecithin for injection | 1.0–3.0 g |
| Glycerin for injection | 1.5–3.0 g |
| Vitamin E | 0–0.15 g |
| Water for injection | to 100 ml |

12. A pharmaceutical composition of claim 11, comprising:

| | |
|---|---|
| Walnut kernel oil for injection | 20 g |
| Soya lecithin for injection | 1.2 g |
| Glycerin for injection | 2.5 g |
| Water for injection | to 100 ml |

13. A pharmaceutical composition of claim 8, comprising:

| | |
|---|---|
| Fluorouracil | 1.0–5.0 g |
| Walnut kernel oil for injection | 5.0–30 g |
| Soya lecithin for injection | 1.0–3.0 g |
| Glycerin for injection | 1.5–3.0 g |
| Vitamin E | 0–0.15 g |
| Water for injection | to 100 ml |

14. A pharmaceutical composition of claim 8, comprising:

| | |
|---|---|
| Fluorouracil | 1.0–5.0 g |
| Walnut kernel oil for injection | 5.0–30 g |
| Soya lecithin for injection | 1.0–3.0 g |
| Glycerin for injection | 1.5–3.0 g |
| Vitamin E | 0–0.15 g |
| Water for injection | to 100 ml |

15. A pharmaceutical composition of claim 7, characterized in that said pharmaceutical composition is a capsule containing a kernel oil extracted from plant kernels, comprising triglycerides 90–99.9%, diglycerides 0.0 1–5%, monoglycerides 0.01–3%, sitosterol 0.1–2.5% and cyclolanosterol 0.01–1%.

16. A method for the treatment of tumors, AIDS, hypoimmunity, infantile malnutrition, post-operation and diseases in need of supplementing fat elements, comprising administering to a subject in need thereof a therapeutically effective amount of a kernel oil according to claim 1.

17. A kernel oil of claim 2, characterized in that the oil is extracted from kernels of spine date, flatspine pricklyash, or walnut.

18. A kernel oil of claim 3, characterized in that the oil is extracted from kernels of spine date, flatspine pricklyash, or walnut.

19. A pharmaceutical composition, comprising a therapeutically effective amount of the kernel oil of claim 2 and one or more pharmaceutically acceptable adjuvants.

20. A pharmaceutical composition, comprising a therapeutically effective amount of the kernel oil of claim 3 and one or more pharmaceutically acceptable adjuvants.

21. A pharmaceutical composition, comprising a therapeutically effective amount of the kernel oil of claim 4 and one or more pharmaceutically acceptable adjuvants.

22. A pharmaceutical composition of claim 7, characterized in that said pharmaceutical composition is a fatty emulsion of a kernel oil characterized in that the lipolysis of said kernel oil gives the following fatty acids: hexadecanoic acid 5–8%, octadecanoic acid 1–3%, octadecenic acid 18–30%, octadecadienoic acid 50–65% and calendic acid 6–14%, and said pharmaceutically acceptable adjuvants include one or more substances selected from a group consists of an emulsifier, a solubiliser, a latent solvent, an isotonic regulator, an antioxidant and an stabilizer.

23. A pharmaceutical composition of claim 7, characterized in that said pharmaceutical composition is a fatty emulsion of a kernel oil characterized in having the following physical properties tested on the basis of fatty oil: relative density 0.920–0.930, refractive index 1.470–1.480, acid value<0.80, iodine value 120.0–155.0, saponification value 180.0–200.0, peroxide value<30.0 meq.kg−1, ignited residue 0.01–0.04%, arsenic salts<2 ppm, heavy metals<10 ppm, and mean molecular weight 873.96, and said pharmaceutically acceptable adjuvants include one or more substances selected from a group consists of an emulsifier, a solubiliser, a latent solvent, an isotonic regulator, an antioxidant and an stabilizer.

24. A pharmaceutical composition of claim 22, said kernel oil is extracted from kernels of spine date, flatspine pricklyash, or walnut.

25. A pharmaceutical composition of claim 23, said kernel oil is extracted from kernels of spine date, flatspine pricklyash, or walnut.

26. A pharmaceutical composition of claim 7, characterized in that said pharmaceutical composition is a capsule containing a kernel oil characterized in that the lipolysis of said kernel oil gives the following fatty acids: hexadecanoic acid 5–8%, octadecanoic acid 1–3%, octadecenic acid 18–30%, octadecadienoic acid 50–65% and calendic acid 6–14%.

27. A pharmaceutical composition of claim 7, characterized in that said pharmaceutical composition is a capsule containing a kernel oil characterized in having the following physical properties tested on the basis of fatty oil: relative density 0.920–0.930, refractive index 1.470–1.480, acid value<0.80, iodine value 120.0–155.0, saponification value 180.0–200.0, peroxide value<30.0 meq.kg−1, ignited residue 0.01–0.04%, arsenic salts<2 ppm, heavy metals<10 ppm, and mean molecular weight 873.96.

28. A pharmaceutical composition of claim 26, said kernel oil is extracted from kernels of spine date, flatspine pricklyash, or walnut.

29. A pharmaceutical composition of claim 27, said kernel oil is extracted from kernels of spine date, flatspine pricklyash, or walnut.

* * * * *

UNITED STATES PATENT AND TRADEMARK OFFICE
CERTIFICATE OF CORRECTION

PATENT NO. : 6,743,930 B2
APPLICATION NO. : 10/123964
DATED : June 1, 2004
INVENTOR(S) : Dapeng Li It is certified that error appears in the above-identified patent and that said Letters Patent is hereby corrected as shown below:

PLEASE ENTER CLAIMS AS FOLLOWS, 1. (Currently Amended) A kernel oil extracted from plant kernels, comprising triglycerides 90-99.9%, diglycerides 0.01-5%, monoglycerides 0.01-3%, sitosterol 0.1-2.5% and cyclolanosterol 0.01-1%; and the lipolysis of said kernel oil gives the following fatty acids: hexadecanoic acid 5-8%, octadecanoic acid 1-3%, octadecenic acid 18-30%, octadeadienoic acid 50-65% and calondic acid 6-14%.

2. (Cancelled).

16. (Currently Amended) A method of the treatment of tumors, AIDS, hypoimmunity, infantile malnutrition, post-operation and diseases in need of supplementing fat elements, comprising administering to a subject in need thereof a therapeutically effective amount of a kernel oil according to claim 1 by itself or in combination with an active drug selected from anti-tumor agents, anti-AIDS agents, immunomodulators and nutrients.

Signed and Sealed this

Twenty-fourth Day of April, 2007

JON W. DUDAS
*Director of the United States Patent and Trademark Office*